United States Patent [19]

Dunn, Jr.

[11] Patent Number: 4,708,710
[45] Date of Patent: Nov. 24, 1987

[54] PARTICLE SEPARATION PROCESS

[75] Inventor: George F. Dunn, Jr., Wenonah, N.J.

[73] Assignee: E. I. Du Pont de Nemours and Company, Wilmington, Del.

[21] Appl. No.: 844,959

[22] Filed: Mar. 27, 1986

[51] Int. Cl.[4] ...................... B01D 21/26; B04B 11/00
[52] U.S. Cl. .................................... 494/37; 210/787; 422/72; 436/45; 494/27
[58] Field of Search ...................... 494/17, 18, 21, 23, 494/27, 28, 29, 37, 45; 422/72, 101; 210/781, 782, 787, 788; 436/45; 604/4, 5, 6

[56] References Cited

U.S. PATENT DOCUMENTS

| | | | |
|---|---|---|---|
| 4,098,456 | 3/1977 | Bayham | 233/14 R |
| 4,268,393 | 5/1980 | Persidsky et al. | 210/516 |
| 4,285,810 | 8/1981 | Kirkland | 494/37 |
| 4,304,357 | 12/1981 | Schoendorfer | 233/26 |
| 4,322,298 | 3/1982 | Persidsky | 210/787 |
| 4,350,283 | 9/1982 | Leonian | 233/26 |
| 4,416,654 | 11/1983 | Schoendorfer et al. | 494/10 |
| 4,464,167 | 8/1984 | Schoendorfer et al. | 604/6 |
| 4,482,636 | 11/1984 | Mochida | 422/72 |
| 4,612,289 | 9/1986 | Furuta | 436/45 |

FOREIGN PATENT DOCUMENTS 2918834 5/1979 Fed. Rep. of Germany .
1313753 7/1970 United Kingdom .

Primary Examiner—Robert W. Jenkins

[57] ABSTRACT

A process for separating particles from mixtures containing the particles is disclosed. An adoptive transfer therapy process wherein mononuclear cells are separated from a mixture of blood cells by the process is also disclosed. The process comprises supporting the mixture in a centrifuge chamber; subjecting the chamber to a centrifugal force; and forcing a displacing fluid through the chamber, against the centrifugal force, thereby separating the preselected particles from the mixture. The process is further characterized in that the displacing fluid has a density greater than or equal to the density of the preselected particles.

32 Claims, 4 Drawing Figures

PARTICLE SEPARATION PROCESS

FIELD OF THE INVENTION

This invention relates to the field of particle separation, and more specifically, a process for separating biological cells from mixtures.

BACKGROUND OF THE INVENTION

Particle separation processes have a diverse variety of applications. Therapeutic techniques being developed in the medical field require efficient blood processing. Cell components of blood are typically separated by centrifugation and/or eleutriation. Improved processes for separating cell populations from blood with a minimum of undesired cell contamination are of interest to the medical field.

The following references disclose methods for separating particles from mixed populations. U.S. Pat. No. 4,350,283 discloses a centrifuge rotor adapted for continuous separation of specific particles from mixed populations thereof, by centrifugal elutriation. The rotor is adapted to be supported on a centrifuge drive shaft and has an elutriating cell housing means with at least two equally spaced apart elongated cavities disposed symmetrically with respect to the axis of rotation of the rotor. A fluid delivery spindle is disposed in the rotor having fluid inlet and outlet passages communicating with each of the elongated cavities of the rotor. An elutriating liquid is pumped through the rotor by an external pump.

G.B. Patent No. 1,313,753 disclosed a method and apparatus for conducting particle size analysis of a particulate solid material. The method comprises introducing a suspension of solid material into a rotating bowl centrifuge and causing an elutriating liquid to flow through the suspension. Elutriated particles are collected in a receiving vessel. The method is described as particularly suitable for separating particles from 0.1 to 5 microns in size from a particulate solid material. The apparatus comprises a reservoir for holding a supply of elutriating liquid, a centrifuging chamber which has an inlet and outlet and a duct means connecting the reservoir with the centrifuging chamber.

DE No. 2,918,384 (Abstract) discloses a modular system for fractionating (separating) biological cells. A cell suspension is fed into a cell disruptor and then through one or several series-connected rotors (e.g., counterflow centrifuges with elutriator/rotor). The separation of cell nuclei, particle fractions, and ribosomes is disclosed. The modular system reduces the path to be traveled by the biological material.

The following references disclose methods and apparatuses for separating blood components. U.S. Pat. No. 4,268,393 discloses an apparatus for separating platelet rich plasma (PRP) from whole blood. A blood sample is placed in a chamber and subjected to centrifugal force. A relatively small volume of saline is injected into the centrifugally outer end of the chamber, whereby PRP is displaced from the chamber into a collection bag. Red and white blood cells are held at a steady state equilibrium in the chamber. In a preferred apparatus, the saline is injected into the blood sample by driving the chamber supporting the blood sample against a saline filled collapsible cavity under the influence of centrifugal force.

U.S. Pat. No. 4,304,357 discloses an apparatus and process for separating blood into a plasma-rich component and a plasma-poor component. A processing bag containing whole blood and a flexible displacement pouch having a fluid operating diaphragm are positioned within a blood processing chamber in a centrifuge rotor. The chamber comprises a pair of contoured support shoes and a pressure plate positioned against the inner wall of the support shoe nearest the center of rotation of the rotor. As displacer fluid is introduced into the displacement pouch, blood or blood components are forced out of the processing bag and collected in a receiver container.

U.S. Pat. Nos. 4,416,654 and 4,464,167 disclose a method and apparatus for separation of specific cells. A two-port centrifugation pheresis bowl is utilized for centrifugation and high speed elutriation. In a particular embodiment, red cell-free platelets are separated from blood by pumping low density fluid, preferably plasma, through centrifugally separated cells to elutriate the cells according to their sedimentation rate.

U.S. Pat. No. 4,322,298 discloses a method and apparatus for the fractionation of a suspension of finely divided solid particles differing in sedimentation velocity. The separation of platelet rich plasma (PRP) from whole blood is accomplished by centrifuging a blood sample and injecting into its outer centrifugal end a volume of saline. The saline displaces PRP from the blood sample after red cells have been sedimented away from the other end of the bag. The preferred apparatus is designed as a closed system of interconnected bags held in a support made to fit a large centrifuge bucket.

U.S. Pat. No. 4,098,456 discloses a centrifuge cup having a mouth-defining rim, a pair of separable cap memberhalves, and means for gripping the upper end of a flexible bag position in the cup. The flexible bag is described as particularly desirable for washing blood and separating blood components. The bag contains an inlet and an outlet, plus a third, sealed port for access to blood cells after centrifugation. Blood cell washing is accomplished by percolating a wash solution through the cells.

U.S. Pat. No. 4,269,718 discloses a method and apparatus for the separation of finely divided solid particles dissimilar in size and/or density, such as platelets and other blood cells. The separation of platelets is accomplished by subjecting a blood sample to centrifugal force in a chamber and injecting a relatively small volume of saline into the centrifugally outer end of the chamber, whereby platelets are displaced from the blood sample. In the preferred apparatus, the saline is injected into the blood sample by driving the chamber supporting the blood sample into a saline filled cavity under the influence of centrifugal force.

These references disclose centrifugal elutriation processes in which particles having different sedimentation characteristics are separated from mixtures. The mixtures are subjected to a centrifugal force while a separating fluid is pumped against the force at a rate greater than the sedimentation rates of the desired particles. The separating fluid is lighter, i.e. less dense, than desired particles. Separated particles are displaced by viscous drag resulting from moving liquid on the surface of the particles. Since small-dense particles can have the same viscous drag effect as larger-less dense particles, elutriation does not effectively separate particles having different densities. In many particle separation processes, particularly of blood cells, separation based on particle density is desirable. The process of the present invention provides improved separation of particles having different densities as compared to eleutriation.

Boyum, *Scandinavian Journal of Clinical and Laboratory Investigations,* 21:77 (1968) discloses the isolation of mononuclear cells and granulocytes from human blood. The reference discloses that when anticoagulated blood was layered on top of a mixture of Isopaque and Ficoll in a centrifuge tube and centrifuged, the cellular elements were divided into two main fractions: granulocytes and erythrocytes sedimented to the bottom of the tube, while mononuclear cells, together with platelets, remained at the interface. The yield of mononuclear cells was said to be almost 100 percent, when the blood was diluted with saline before centrifugation. In the process of the present invention, mononuclear cells can be separated from a mixture of blood cells in a closed apparatus and without dilution prior to separation.

SUMMARY OF THE INVENTION

The present invention provides a process for separating preselected particles from a mixture containing the particles. The mixture is supported in a centrifuge chamber and the chamber is subjected to a centrifugal force. A displacing fluid is forced through the chamber against the centrifugal force, thereby separating the preselected particles from the mixture. The displacing fluid has a density greater than or equal to the density of the preselected particles. The invention also provides an improved adoptive transfer therapy process wherein mononuclear cells are separated from a mixture of blood cells according to the specified process.

DETAILED DESCRIPTION OF THE INVENTION

Figure 1:
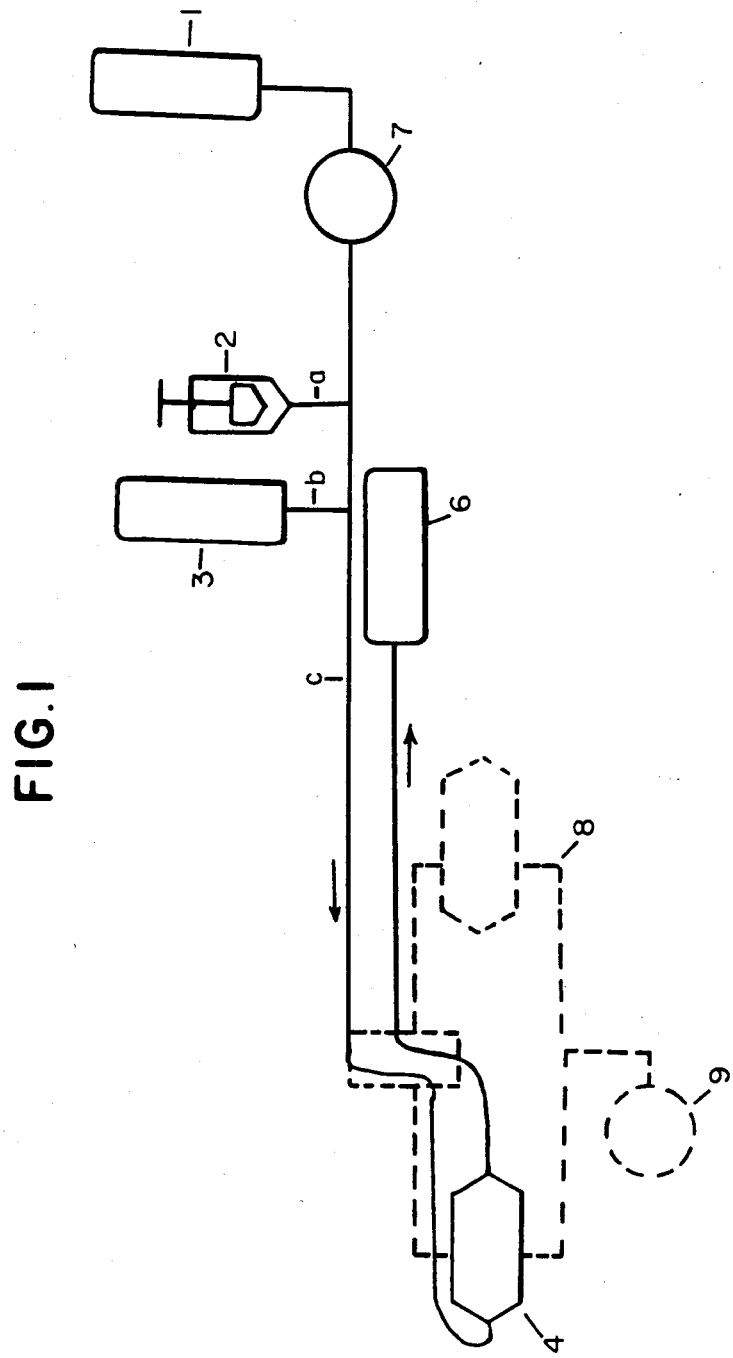
FIG. 1 shows a stylized representation of an apparatus used for separating mononuclear cells from a mixture of blood cells.

The present process separates preselected particles from a mixture containing the particles based on the relative densities of particles in the mixture. As used herein, "preselected particles" means the particles which are to be separated from denser components of the mixture. The term "mixture" refers to a combination of two or more types of solid or semi-solid particles in varying proportions. The size of the particles in the mixture is not critical. Preferably, the preselected particles have a diameter of from about 1 $\mu$m to about 0.25 cm, and most preferably from about 2 $\mu$m to about 20 $\mu$m. A partial list of suitable particles for separation in the present process includes biological cells, ground ore, catalyst particles, and polymer particles. In a preferred embodiment, the preselected particles are biological cells, and most preferably blood cells.

It has been found that the process of the present invention effectively separates mononuclear cells from mixtures of blood cells. The expression "mononuclear cells" refers to lymphocytes and monocytes. Mononuclear cells are known to include lymphocytes which can be treated with a lymphokine, interleukin-2 (IL-2), to generate lymphokine-activated killer (LAK) cells with antitumor reactivity. Whole blood and processed blood fractions are suitable mixtures for the separation of mononuclear cells. Preferably, mononuclear cells are separated from a leukocyte-rich blood cell mixture prepared by centrifugation of whole blood.

The mononuclear cells separated in the present process have a minimum of undesired cell contamination and are useful in an adoptive transfer therapy process as disclosed in Rosenberg, *Journal of the National Cancer Institute,* 75(4):595 (1985) and Rosenberg et al., *New England Journal of Medicine,* 313(23):1485 (1985), the relevant disclosures of which are incorporated herein by reference. Mononuclear cells separated from a mixture of blood cells according to the present process are contacted with a lymphokine, IL-2, to activate lymphokine-activated killer (LAK) cells in the mononuclear cells and generate lymphokines with antitumor reactivity. The activated LAK cells can be introduced into tissue to suppress tumor growth. Another advantage of the process is that blood cells can be separated in a large volume without dilution.

In the present process, the mixture is supported in a centrifuge chamber. As used herein, the expression "supported" means that the particles are held in a centrifuge chamber. Preferably, the particles are mixed with a supporting fluid which enhances the mobility of the particles in the mixture. The supporting fluid should be compatible with the particles in the mixture and have a density less than the density of the preselected particles. Mixtures of cells, like blood cells, can be supported in a variety of liquids including saline solutions, buffered saline solutions and other non-cytotoxic fluids with an osmotic pressure that is similar to that of the natural environment of the selected cells. Plasma provides a suitable supporting liquid for separating blood cells. In one embodiment of the present process, the mixture is introduced into the centrifuge chamber while the chamber is being subjected to a centrifugal force. In this embodiment, the mixture should be introduced at a rate such that turbulence in the chamber is minimized.

Suitable centrifuge chambers are containers to which centrifugal force can be applied. A variety of suitable centrifuge chambers are well known in the art. The process of the invention can be conducted in cylindrical-, conical-, toroidal-shaped chambers, or other chambers lacking irregularities which would adversely affect the desired particle separation. The chamber should have a means for introducing material into the outer centrifugal end and a means for passing material out through the inner centrifugal end. Preferably, the centrifuge chamber is a toroidal-shaped chamber.

The chamber is subjected to a centrifugal force. The amount of centrifugal force is not critical. The force should be sufficient to minimize the effect of the displacing fluid on particles having a density greater than the displacing fluid while allowing the preselected particles to float against the centrifugal force away from denser components of the mixture. Preferably, when mononuclear cells are separated from a mixture of blood cells, the centrifugal force is from about 100$\times$g to about 15,000$\times$g, and most preferably from about 400$\times$g to about 2,000$\times$g. The centrifugal force is effected by rotating the chamber in a centrifuge rotor. A variety of suitable centrifuge rotors are known in the art.

In the present process, a displacing fluid is forced through the chamber, against the centrifugal force, thereby separating the preselected particles from the mixture. The displacing fluid has a density greater than or equal to the density of the preselected particles. Preselected particles having a density equal to or less than the density of the selected displacing fluid are floated against the centrifugal force away from denser components of the mixture. The displacing fluid should be substantially uniform in density and compatible with the preselected particles. Preferably, the displacing fluid has a density equal to or greater than the density of the preselected particles and less than denser components of the mixture. In a preferred embodiment, the mixture is subjected to a centrifugal force to stratify the mixture before the displacing fluid is forced through the chamber against the centrifugal force. The expression "stratify the mixture" means separate the particles supported in the centrifugal chamber into layers or strata according to their respective densities.

A partial list of displacing fluids suitable for the separation of biological cells includes colloidal suspensions, high molecular weight salt solutions, mixtures of polymers with high molecular weight salts, mixtures of polysaccharides with high molecular weight salts and other biologically inert solutions having a desired density. Preferably, biological cells are separated using a mixture of a polysaccharide having a molecular weight of 400,000 and sodium diatrizoate available from A.B. Pharmacia, Uppsala, Sweden under the registered trademark Ficoll-Paque. Preferred displacing fluids for separating mononuclear cells from mixtures of blood cells have a density of from about 1.06 g/mL to about 1.08 g/mL, and most preferably from about 1.07 g/mL to about 1.08 g/mL.

The rate at which the displacing fluid is forced through the chamber, against the centrifugal force, is not critical. The rate should be such that the desired separation is effected in a reasonable amount of time without causing excessive turbulence in the chamber. The rate should also be such that the linear velocity of particles in the mixture having a density greater than the displacing fluid is sufficiently less than the linear velocity of the displacing fluid to effect the desired separation. "Linear velocity" refers to the rate at which materials move away from the outer centrifugal end of the centrifuge chamber toward the inner centrifugal end of the chamber. Preferably, the rate is less than that necessary to effect a positive linear velocity on particles in the mixture having a density greater than the density of the displacing fluid. Suitable means for forcing the displacing fluid through the chamber include pumping and differential pressure caused by centrifugal force or gravity. After the desired separation is effected, the preselected particles having a density less than or equal to the selected displacing fluid are collected. Preferably, these particles are collected as they pass out of the inner centrifugal end of the centrifuge chamber.

The present process can be conducted in batch mode, continuous mode, or a combination thereof. Preferably, the process is conducted in a closed apparatus, and most preferably a closed apparatus comprising a centrifuge chamber and storage bags connected by tubing. The apparatus includes or is capable of being connected to a means for forcing the displacing fluid through the centrifuge chamber. The apparatus is placed in a centrifuge rotor which contains a plurality of cavities capable of enclosing the chamber and storage bags. The rotor can also have a means for forcing the displacing fluid through the chamber. Preferably, the means is a peristatic pump and the apparatus is compatible with sterile connection devices.

The process of the present invention is further described in the following examples wherein all parts and percentages are by number and degrees are Celsius, unless otherwise stated. The following specific gravity ranges are reported for normal human blood cells in Sanderson, *Cell Separation: Methods and Selected Applications*. Vol. 1, (Academic Press, Inc. 1982): lymphocytes from 1.065 to 1.075 g/mL; monocytes from 1.058 to 1.068 g/mL; granulocytes from 1.078 to 1.09 g/mL; and red cells from 1.04 to 1.1 g/mL. Cytotoxicity for tumor cells of IL-2 treated mononuclear cells was determined substantially as disclosed in *Selected Methods in Cellular Immunology*, ed. B. B. Mishell et al. (W. H. Freeman, San Francisco, 1980) at 134–137, the relevant disclosure of which is incorporated herein by reference, according to the following procedure.

LAK Activity Assay

A four hour $^{51}Cr$ release assay was used to measure cytotoxicity of the IL-2 treated mononuclear cells. Mononuclear cells were suspended to $1\times10^6$ cells/mL in a cell culture media containing RPMI 1640, a buffered solution available commercially from M.A Bioproducts, Walkersville, Md.; 1% (by volume) of Penstrep, a penicillin and stryptomycin composition available commercially from Gibco Co., Grand Island, N.Y.; 1% (by volume) glutamine; 1% (by volume) of ABM, an antibiotic and antimycotic composition available commercially from Gibco Co.; and 20 millimolar of HEPES, a $CO_2$ buffer available commercially from Gibco Co. The cell culture media was combined with 1500 picomolar recombinant IL-2 and 10% (by volume) human serum. The resulting mixture was incubated at 37° for 3 to 5 days. After the incubation period, nonadherent cells were harvested and resuspended in the cell culture media described above supplemented with 10% (by volume) human serum.

Two million Burkitt lymphoma cells (Raji, ATCC CCL 86) were incubated with 50 μCi of $Na_2^{51}CrO_2$ in 0.4 mL of tris-phosphate buffered saline for 1 hour at 37° C. The cells were then washed 4 times with the buffered solution (RPMI 1640) described above containing 5% (by volume) fetal calf serum and resuspended to a concentration of $10^5$ cells/mL in the buffered solution (RPMI-1640) with 10% (by volume) human serum. The IL-2 treated mononuclear cells and the $^{51}Cr$ treated lymphoma cells were added to round bottom microtiter plates to cell ratios of 5:1, 20:1, and 50:1 (mononuclear:lymphoma). The plates were centrifuged at 200×g for 5 minutes, incubated at 37° for 4 hours, and centrifuged again at 200×g. 0.1 mL of the resulting supernatants were removed from each well and counted in a gamma counter. The supernatant of $^{51}Cr$ treated lymphoma cells which were not combined with the IL-2 treated mononuclear cells and lysed $^{51}Cr$ treated lymphoma cells were also counted in a gamma counter. Percent toxicity was calculated from the following formula, wherein "experimental cpm" means the counts per minute of the supernatant from the combination of IL-2 treated mononuclear cells and the $^{51}Cr$ treated lymphoma cells, "spontaneous cpm" means the counts per minute of the supernatant of the $^{51}Cr$ treated lymphoma cells, and "total cpm" means the counts per minute of the supernatant of the lysed $^{51}Cr$ treated lymphoma cells.

$$\% \text{ cytoxicity} = \frac{(\text{experimental } cpm - \text{spontaneous } cpm) \times 100}{\text{total } cpm - \text{spontaneous } cpm}$$

In Examples 4, 5, and 6 and Comparative Experiments A, B, and C cytotoxicity was determined in triplicate.

EXAMPLE 1

Mononuclear cells were separated from a mixture of blood cells in a cylindrical centrifual chamber having an inside diameter of about 2 inches. Each end of the chamber was conically-shaped such that the straight side distance of the chamber was about 3.6 in and the end-to-end distance was about 4.6 in. The chamber was filled with sterile phosphate-buffered-saline solution and subjected to a centrifugal force of about 900×g. 40 mL of a leukocyte-rich blood cell mixture, which had been prepared from about 450 mL of whole blood by centrifugation, were pumped into the outer centrifugal end of the chamber using a syringe. The leukocyte-rich blood cell mixture contained about $2 \times 10^{11}$ red blood cells and about $2$–$4 \times 10^9$ white cells. The white cell population contained about $1$–$2 \times 10^9$ granulocytes, about $0.8$–$1.6 \times 10^9$ lymphocytes, and less than about $0.2$–$0.4 \times 10^9$ monocytes. By means of a window in the top of the centrifuge and a strobe light beneath the chamber, the mixture could be seen to remain in the outer end of the chamber.

As soon as the pumping of the cell mixture was completed, a mixture of a polysaccharide having a molecular weight of 400,000 and sodium diatrizoate, commercially available from A.B. Pharmacia, Uppsala, Sweden under the tradename Ficoll-Paque, was pumped into the outer end of the chamber at a rate of 4 mL/min by means of a peristatic pump. The polysaccharide and sodium diatrizoate mixture had a density of 1.077 g/mL. After pumping the polysaccharide and sodium diatrizoate mixture for seven minutes, a distinct cell layer separated from the rest of the mixture. This pumping was continued until the cell layer was forced out of the inner centrifugal end of the chamber. Samples being forced out of the inner end of the chamber were collected and analyzed for white cell content. The results are shown in Table 1.

TABLE 1

| Sample | Volume (mL) | Density (g/mL) | Total White Cells |
|---|---|---|---|
| 1 | 13 | N.D. | $1.3 \times 10^9$ |
| 2 | 5 | 1.071 | $5.2 \times 10^7$ |
| 3 | 20 | 1.073 | $7.2 \times 10^7$ |
| 4 | 25 | 1.073 | $6.4 \times 10^7$ |
| 5 | 22 | 1.074 | $1.6 \times 10^7$ |
| 6 | 35 | 1.074 | $2.8 \times 10^7$ |

N.D.—not determined

Sample 1 was found to contain about 85% of the white cells collected and comprised 100% mononuclear cells having 65% lymphocytes, 17% monocytes, and 13% large granular lymphocytes. The residue from the centrifugation chamber was found to comprise about 100% granulocytes and red blood cells.

EXAMPLE 2

The procedure described in Example 1 was substantially repeated except that the polysaccaride and sodium diatrizoate mixture was not pumped into the chamber until after the mixture of blood cells had stratified into layers of plasma, white cells, and red cells (about 10 min). The centrifugal force was about 900×g and the polysaccaride and sodium diatrizoate mixture was added at a rate of 4.5 mL/min. Samples being forced out of the inner end of the chamber were collected and analysed for white cell content. The results are shown in Table 2.

TABLE 2

| Sample | Volume (mL) | Density (g/mL) | Total White Cells |
|---|---|---|---|
| 1 | 15 | 1.029 | $2.6 \times 10^6$ |
| 2 | 7.5 | 1.066 | $1.06 \times 10^9$ |
| 3 | 19 | 1.073 | $1.13 \times 10^8$ |
| 4 | 17 | N.D. | $1.04 \times 10^8$ |
| 5 | 22 | 1.074 | $1.62 \times 10^8$ |
| 6 | 20 | N.D. | $1.18 \times 10^8$ |

N.D.—not determined

The Samples were found to comprise the white cell contents shown in Table 3.

TABLE 3

| Sample | Mononuclear Cell (%) | White Cell Content |
|---|---|---|
| 1 | 100 | 76% lymphocytes, 24% monocytes; |
| 2 | 100 | 91% lymphocytes, 8% monocytes, 1% large granular lymphocytes; |
| 3 | 94 | 70% lymphocytes, 8% monocytes, 11% large granular lymphocytes, 1% eosinophiles, 5% undetermined; |
| 4 | 37 | 29% lymphocytes, 13% monocytes, 60% segmented neutrophiles, 1% eosinophiles, 2% undetermined; |
| 5 | 9 | 8% lymphocytes, 1% monocytes, 90% segmented neutrophiles, 1% eosinphiles; |
| 6 | 0 | 100% segmented neutrophiles. |

EXAMPLE 3

Mononuclear cells were separated from a 45 mL sample of concentrated blood cells according to a procedure similar to that described in Example 2. The sample, which had a cell population of 15% lymphocytes, 2% monocytes, and 83% granulocytes, was pumped into the centrifuge chamber and stratified into layers of plasma, white cells, and red cells (about 20 min). The centrifugal force was about 900×g and the polysaccharide and sodium diatrizoate mixture was added at a rate of about 5.6 mL/min. After 118 mL of the polysaccharide and sodium diatrizoate mixture had been pumped into the centrifuge tube, plasma began being forced out of the inner end of the chamber. After an additional 14 mL of the polysaccharide and sodium diatrizoate mixture were pumped into the chamber, cells began being forced out of the inner end of the chamber. An additional 19 mL of the polysaccharide and sodium diatrizoate mixture were pumped into the chamber and the resulting centrifuge exodate was collected. A differential white count on the centrifuge exodate showed a cell population of 88% lymphocytes, 9% monocytes, 2% large granular lymphocytes, and 1% granulocytes. A total of $1.1 \times 10^9$ blood cells were collected.

EXAMPLE 4

Mononuclear cells were separated from a mixture of blood cells and plasma from leukphoresis in the apparatus shown in FIG. 1. Replaceable feed bags (1 and 3) were connected to the outer centrifugal end of a centrifuge chamber (4) by tubing. A 60 mL syringe (2) and a peristatic pump (7) were connected to the tubing between the replaceable feed bags (1 and 6). A replaceable collection bag (6) was connected to the inner centrifugal end of the centrifuge chamber (4) by tubing.

Centrifuge chamber (4) was replaced with a bypass line and feed bag (3) was disconnected from the apparatus. The resulting apparatus was sterilized by passing a solution of 6% (by volume) hydrogen peroxide from feed bag (1) to collection bag (6). A sterile saline solution was then passed from feed bag (1) to collection bag (6) to remove hydrogen peroxide from the apparatus. Centrifuge chamber (4) was sterilzed, flushed with saline, connected to the apparatus, and placed in a centrifuge rotor (8) in a centrifuge (9). A feed bag containing 190 mL of a mixture of blood cells and plasma from leukophoresis, designated Sample A, was sterilely connected as feed bag (3) and the tubing was closed at point b. The centrifuge (9) was started and the apparatus was deaerated by introducing sterile saline into the apparatus from feed bag (1) using the peristatic pump (7) and the 60 mL syringe (2) as pumping sources.

With the syringe plunger down, the peristatic pump (7) turned off, points a and b open, and point c closed, the plunger was raised to to draw about 50 mL of the blood cell mixture into the syringe (2). Point b was then closed, point c was opened, and the mixture in the syringe (2) was injected into the apparatus. Blood cells were seen entering the centrifuge chamber (4). This procedure was repeated until substantially the entire mixture had been injected into the centrifuge chamber (4). The cells were allowed to settle for about 10 minutes. During this time, a bag containing 250 mL. of a polysaccaride and sodium diatrizoate mixture similar to that described in Example 1 having a density of 1.075 was attached to the apparatus as feed bag (1). The polysaccaride and sodium diatrizoate mixture was pumped to point c in order to clear the tubing of the saline solution. The polysaccaride and sodium diatrizoate mixture was then pumped into the centrifuge chamber (4) at a rate of 4 mL/min while the chamber (4) was being subjected to a centrifugal force of about 900×g. After about 135 mL of the polysaccaride and sodium diatrizoate mixture were pumped into the chamber (4), collection bag (6) which contained a mixture of saline and plasma was replaced with a sterile bag to collect subsequent fractions. About 45 mL of sample, designated Sample B, were collected in bag (6) and analyzed for white cell content. The results are shown in Table 4.

TABLE 4

| Sample | Red Cells | White Cells | Cell Content (White Cells) |
|---|---|---|---|
| A | $1.2 \times 10^{11}$ | $7.7 \times 10^9$ | 58% lymphocytes, 37% monocytes, 5% granulocytes |
| B | $5.0 \times 10^8$ | $4.8 \times 10^9$ | 83% lymphocytes, 16% monocytes, 1% granulocytes |

Figure 2:
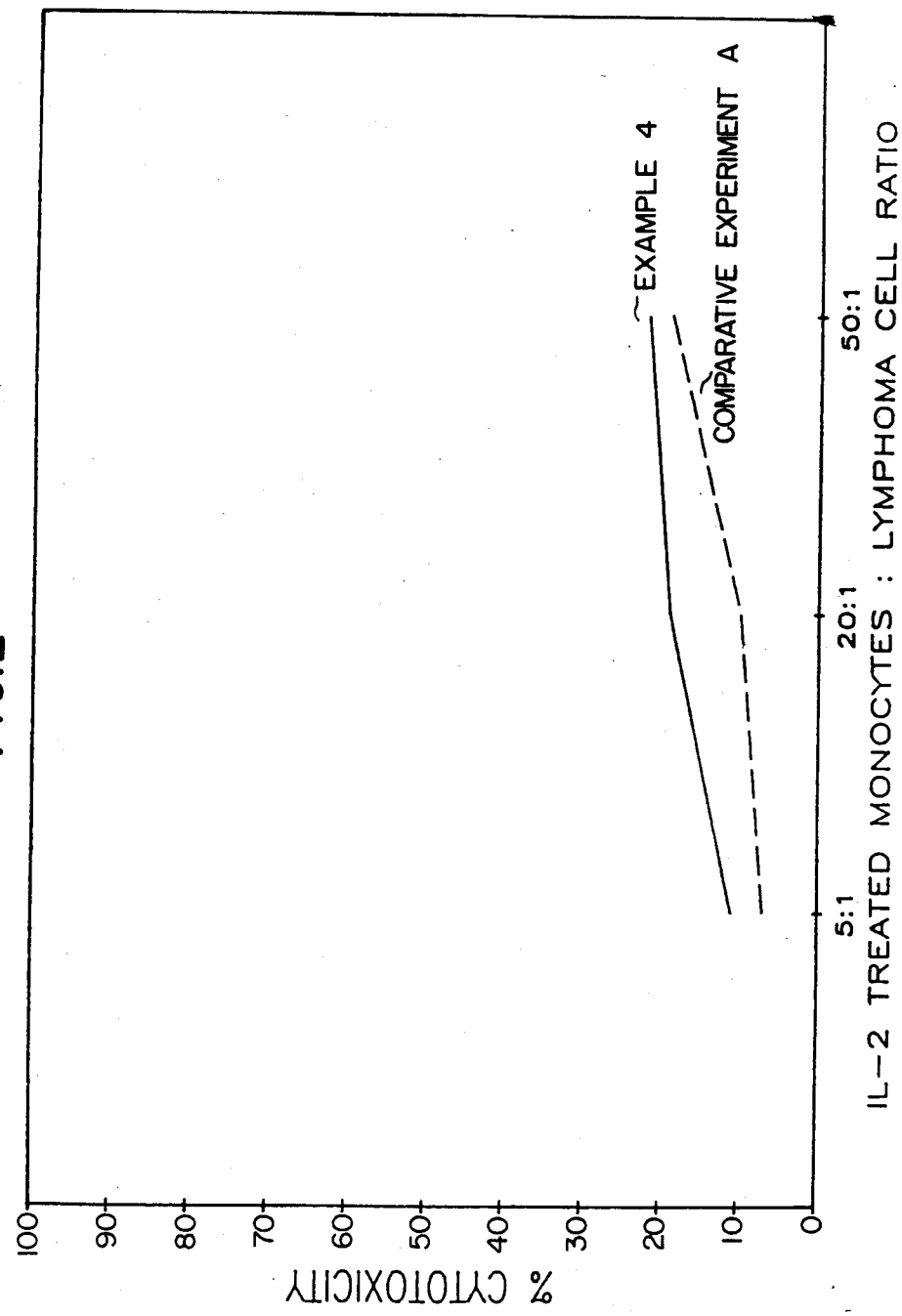
FIGS. 2, 3, and 4 show the cytotoxicity for tumor cells of IL-2 (interleukin-2) treated mononuclear cells separated from mixtures of blood cells.

LAK activity of Sample B after incubation in IL-2 for 3 days was determined and the results are shown in Table 5 and FIG. 2.

COMPARATIVE EXPERIMENT A 10 mL of the mixture of blood cells and plasma from leukophoresis used in Example 4 were diluted (1:1 by volume) with Seligmann's Balanced Salt Solution (SBSS), a sterile saline solution available commercially from Gibco Co. and layered on 20 mL of the polysaccaride and sodium diatrizoate mixture described in Example 4 in a 50 mL centrifuge tube. The centrifuge tube was subjected to a centrifugal force of about 400×g for about 25 minutes. A layer of cells at the interface between the saline and the polysaccaride and sodium diatrizoate mixture was collected by pipetting and washed in 3 times in the sterile saline solution described above at 400×g for 10 minutes, at 200×g for 10 minutes, and at 200×g for 10 minutes. LAK activity of the resulting cells after incubation in IL-2 for 3 days was determined and the results are shown in Table 5 and FIG. 2.

EXAMPLE 5

Figure 3:
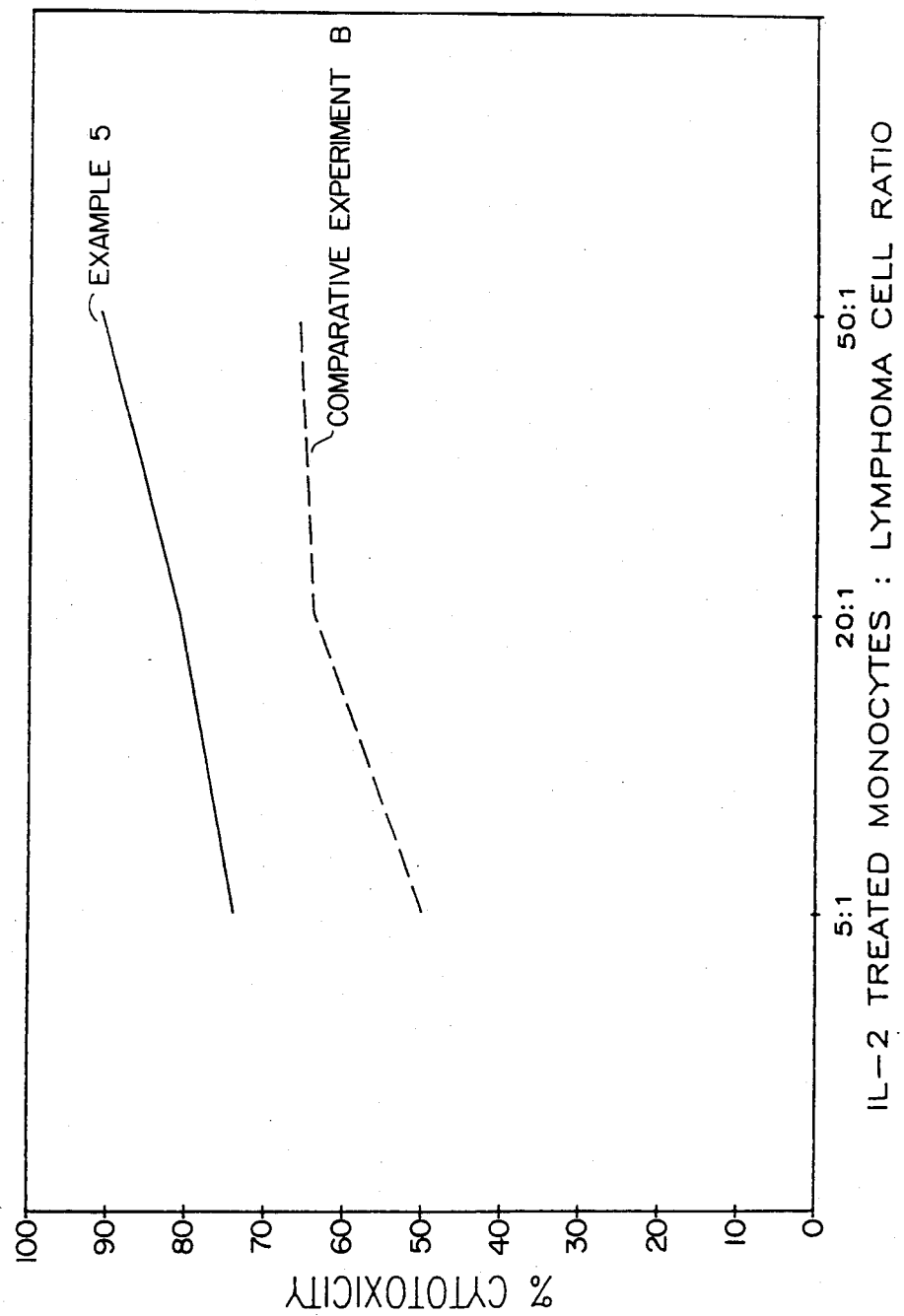

The procedure described in Example 4 was substantially repeated with 154 mL of mixture of blood cells and plasma from leukophoresis. During separation the mixture was subjected to a centrifugal force of about 100×g. LAK activity of the resulting cells after incubation in IL-2 for 5 days was determined and the results are shown in Table 5 and FIG. 3.

COMPARATIVE EXPERIMENT B

The procedure described in Comparative Experiment A was substantially repeated using 10 mL of the mixture of blood cells and plasma from leukophoresis used in Example 5. LAK activity of the resulting cells after incubation in IL-2 for 5 days was determined and the results are shown in Table 5 and FIG. 3.

EXAMPLE 6

Figure 4:
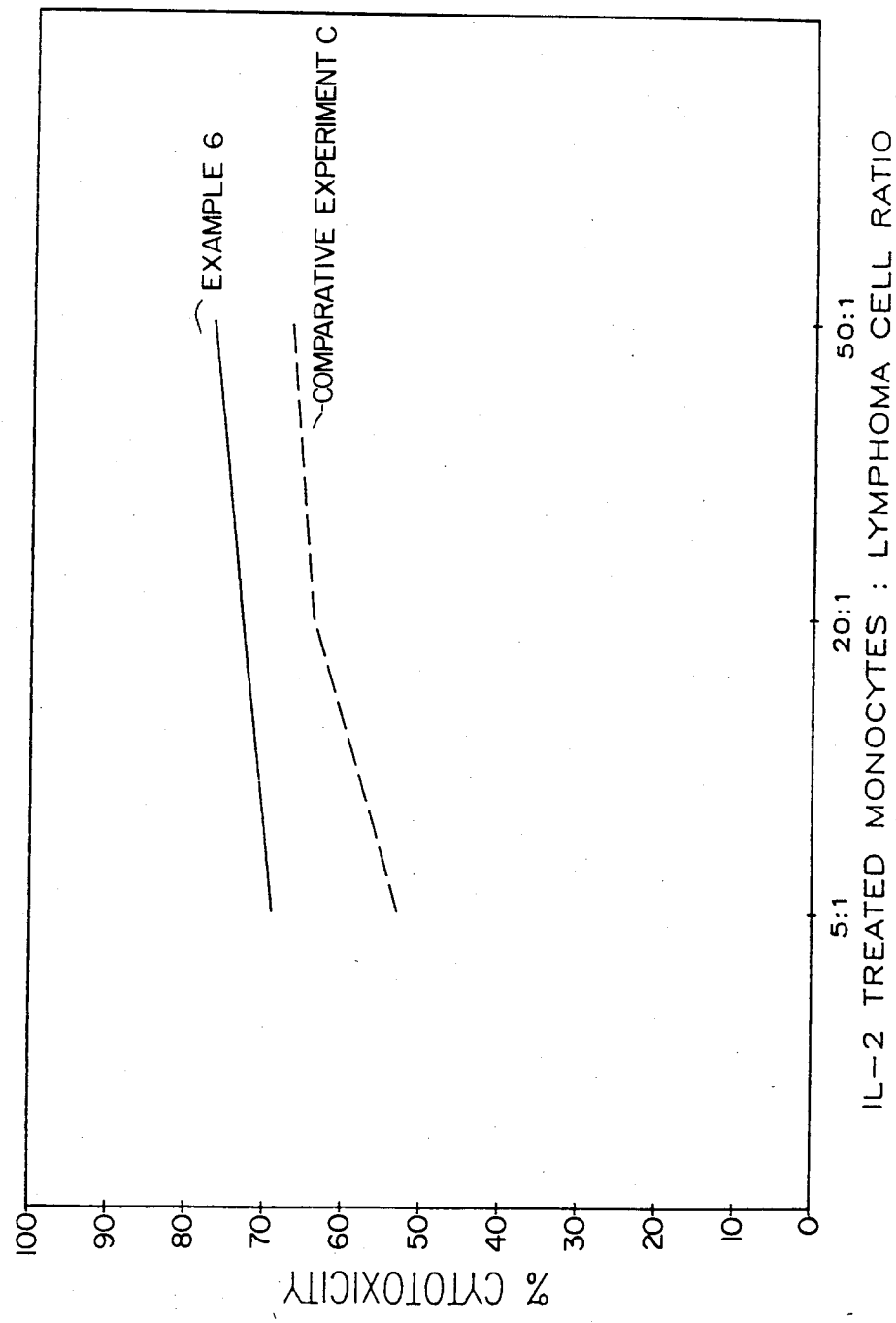

The procedure described in Example 4 was substantially repeated with 185 mL of mixture of blood cells and plasma from leukophoresis. During separation the mixture was subjected to a centrifugal force of about 100×g. LAK activity of the resulting cells after incubation in IL-2 for 4 days was determined and the results are shown in Table 5 and FIG. 4.

COMPARATIVE EXPERIMENT C

The procedure described in Comparative Experiment A was substantially repeated using 10 mL of the mixture of blood cells and plasma from leukophoresis used in Example 5. LAK activity of the resulting cells after incubation in IL-2 for 4 days was determined and the results are shown in Table 5 and FIG. 4.

TABLE 5

| | Cytotoxicity for Tumor Cells of IL-2 Treated Mononuclear Cells | |
|---|---|---|
| Example or Comp. Exp. | IL-2 Treated Mononuclear:Lymphoma Cell Ratio | % $^{51}$Cr Released |
| 4 | 50:1 | 22 |
| | 20:1 | 19 |
| | 5:1 | 11 |
| A | 50:1 | 19 |
| | 20:1 | 10 |
| | 5:1 | 7 |
| 5 | 50:1 | 91 |
| | 20:1 | 81 |
| | 5:1 | 74 |
| B | 50:1 | 66 |
| | 20:1 | 64 |
| | 5:1 | 50 |
| 6 | 50:1 | 77 |
| | 20:1 | 73 |
| | 5:1 | 69 |
| C | 50:1 | 67 |
| | 20:1 | 64 |
| | 5:1 | 53 |

What is claimed is:
1. A process for separating preselected particles from a mixture containing the particles, comprising:
supporting the mixture in a centrifuge chamber;
subjecting the chamber to a centrifugal force; and forcing a displacing fluid through the chamber, against the centrifugal force, thereby separating the preselected particles from the mixture;

wherein the displacing fluid has a density greater than or equal to the density of the preselected particles.

2. A process as defined in claim 1, wherein the mixture is subjected to a centrifugal force to stratify the mixture before the displacing fluid is forced through the chamber against the centrifugal force.

3. A process as defined in claim 1, wherein the preselected particles have a diameter of from about 1 μm to about 0.25 cm.

4. A process as defined in claim 3, wherein the preselected particles have a diameter of from about 2 μm to about 20 μm.

5. A process as defined in claim 1, wherein the preselected particles are biological cells.

6. A process as defined in claim 5, wherein the displacing fluid is selected from the group consisting of colloidal suspensions, high molecular weight salt solutions, mixtures of polymers with high molecular weight salts, and mixtures of polysaccharides with high molecular weight salts.

7. A process as defined in claim 6, wherein biological cells having a density less than or equal to the displacing fluid are collected as said biological cells pass out of the inner centrifugal end of the centrifuge chamber.

8. A process as defined in claim 5, wherein the process is conducted in a closed apparatus comprising a centrifuge chamber and storage bags connected by tubing.

9. A process as defined in claim 1, wherein the preselected particles are blood cells.

10. A process as defined in claim 9, wherein the blood cells are mononuclear cells.

11. A process as defined in claim 10, wherein the displacing fluid is a mixture of a polysaccharide with a high molecular weight salt.

12. A process as defined in claim 10, wherein the displacing fluid has a density of from about 1.06 g/mL to about 1.08 g/mL.

13. A process as defined in claim 12, wherein the displacing fluid has a density of from about 1.07 g/mL to about 1.08 g/mL.

14. A process as defined in claim 13, wherein the process is conducted in a closed apparatus comprising a centrifuge chamber and storage bags connected by tubing.

15. A process as defined in claim 13, wherein mononuclear cells having a density less than or equal to the displacing fluid are collected as said mononuclear cells pass out of the inner centrifugal end of the centrifuge chamber.

16. A process as defined in claim 12, wherein the centrifugal force is from about 100×g to about 15,000×g.

17. A process as defined in claim 16, wherein the centrifugal force is from about 400×g to about 2,000×g.

18. A process as defined in claim 9, wherein the process is conducted in a closed apparatus comprising a centrifuge chamber and storage bags connected by tubing.

19. A process as defined in claim 10, wherein the process is conducted in a closed apparatus comprising a centrifuge chamber and storage bags connected by tubing.

20. In an adoptive transfer therapy process wherein mononuclear cells are contacted with a lymphokine to activate lymphokine-activated killer cells in the mononuclear cells, the improvement comprising separating said mononuclear cells from a mixture of blood cells by the process comprising:

supporting the mixture of blood cells in a centrifuge chamber;

subjecting the chamber to a centrifugal force; and forcing a displacing fluid through the chamber, against the centrifugal force, thereby separating mononuclear cells from the mixture;

wherein the displacing fluid has a density greater than or equal to the density of the mononuclear cells.

21. A process as defined in claim 20, wherein the mixture of blood cells is subjected to a centrifugal force to stratify the mixture before the displacing fluid is forced through the chamber against the centrifugal force.

22. A process as defined in claim 20, wherein the displacing fluid is a mixture of a polysaccharide with a high molecular weight salt.

23. A process as defined in claim 22, wherein the displacing fluid has a density of from about 1.06 g/mL to about 1.08 g/mL.

24. A process as defined in claim 23, wherein the displacing fluid has a density of from about 1.07 g/mL to about 1.08 g/mL.

25. A process as defined in claim 23, wherein the centrifugal force is from about 100×g to about 15,000×g.

26. A process as defined in claim 25, wherein the centrifugal force is from about 400×g to about 2,000×g.

27. A process as defined in claim 26, wherein the process is conducted in a closed apparatus comprising a centrifuge chamber and storage bags connected by tubing.

28. A process as defined in claim 25, wherein the process is conducted in a closed apparatus comprising a centrifuge chamber and storage bags connected by tubing.

29. A process as defined in claim 23, wherein mononuclear cells having a density less than or equal to the displacing fluid are collected as said mononuclear cells pass out of the inner centrifugal end of the centrifuge chamber.

30. A process as defined in claim 29, wherein the process is conducted in a closed apparatus comprising a centrifuge chamber and storage bags connected by tubing.

31. A process as defined in claim 23, wherein the process is conducted in a closed apparatus comprising a centrifuge chamber and storage bags connected by tubing.

32. A process as defined in claim 20, wherein the process is conducted in a closed apparatus comprising a centrifuge chamber and storage bags connected by tubing.

* * * * *